United States Patent [19]

Horikoshi et al.

[11] Patent Number: 4,624,922

[45] Date of Patent: Nov. 25, 1986

[54] PLASMID, METHOD FOR CONSTRUCTION OF THE SAME, MICROORGANISM CARRYING THE PLASMID AND METHOD FOR CULTIVATION OF THE MICROORGANISM

[75] Inventors: Koki Horikoshi; Toshiaki Kudo, both of Tokyo; Hiroshi Honda, Hino, all of Japan

[73] Assignee: Rikagaku Kenkyusho, Wako, Japan

[21] Appl. No.: 590,636

[22] Filed: Mar. 19, 1984

[30] Foreign Application Priority Data

Dec. 9, 1983 [JP] Japan .............................. 58-232507
Dec. 9, 1983 [JP] Japan .............................. 58-232508

[51] Int. Cl.$^4$ .................. C12N 15/00; C12N 1/00; C12N 1/20; C12P 19/34
[52] U.S. Cl. ............................. 435/172.3; 435/317; 435/91; 435/253; 435/200; 935/14; 935/29; 935/48; 935/56; 935/73
[58] Field of Search ................. 435/172.3, 68, 317; 935/22, 23, 29, 55

[56] References Cited

PUBLICATIONS

Horikoshi et al, 1973, "Xylanase Produced by Alkalophilic Bacillus, No. C-59-2", *Agr. Biol. Chem.*, vol. 37(9), 2097-2103.
Panbangred et al, 1983, "Molecular Cloning of the Genes for Xylan Degradation of *Bacillus pumilus* . . . " *Mol Gen Genet*, vol. 192, pp. 335-341.
Panbangred et al, 1984, "Isolation of Two β-Xylosidase Genes of *Bacillus pumilus* and Comparison of Their Gene Prod.", *E.J. Bioch*, vol. 138, pp. 267-273.
Honda et al, 1985, "Molecular Cloning and Expression of the Xylanase Gene of Alkalophilic Bacillus sp . . . ", *J.Bact*, vol. 161(2), pp. 784-785.
Bernier, Jr. et al, 1983, "Molecular Cloning of a *Bacillus subtilis* Xylanase Gene in *E. coli*", *Gene*, vol. 26, pp. 59-65.

*Primary Examiner*—Thomas G. Wiseman
*Assistant Examiner*—Joanne Giesser
*Attorney, Agent, or Firm*—Bucknam and Archer

[57] ABSTRACT

A novel plasmid pCX311, which was constructed from *Bacillus* sp. C125 chromosomal DNA carrying the gene for extracellular production of xylanase and a vector plasmid pBR322. A novel microorganism, *Escherichia coli* HB101 (pCX311) carrying the plasmid pCX311 and being capable of extracellular production of xylanase. Method for culturing the microorganism characterized by cultivation of it in the medium containing NaCl (or KCl) and bran, or NaCl (or KCl) and xylan for 12-48 hours. According to this invention, useful high-molecular substances can be produced in a high yield.

15 Claims, 5 Drawing Figures

——— : pBR 322 PLASMID DNA

▨▨▨▨ : <u>BACILLUS</u> C125 DNA FRAGMENT
(XYLANASE DNA FRAGMENT)

PLASMID, METHOD FOR CONSTRUCTION OF THE SAME, MICROORGANISM CARRYING THE PLASMID AND METHOD FOR CULTIVATION OF THE MICROORGANISM

BACKGROUND OF THE INVENTION (1) Field of the Invention

This invention relates to a novel plasmid, a method for construction of the plasmid, a novel microorganism containing the plasmid, and a method for cultivation of the microorganism and relates more particularly to a novel plasmid with DNA coding for extracellular production of such high-molecular substances as xylanase, a novel microorganism transformed with the plasmid, and a method for extracellular production of such high-molecular substances as xylanase by culturing the microorganism.

(2) Description of the Prior Art

Plasmid is a non-chromosomal gene of cyclic DNA found in a microorganism cell. Plasmid is currently being used as a means for recombination of microorganism gene and it is becoming more and more important in the field of fermentation industry.

Studies have recently been done on plasmids carrying foreign DNA having genetic information of metabolic products or specific demand for growth of microorganism, as shown in production of amino acids or peptides. Some plasmids have been introduced into host microorganisms to obtain transformants. Methods have been proposed for producing relatively low molecular compounds such as aminoacids and peptides by culturing the transformants. However, the degree of propagation of plasmids carrying genes for production of high-molecular substances depends on the nature of host microorganisms and those plasmids have not effectively been expressed. Furthermore, no effective methods for cultivation of such transformants have been established.

It has not been possible to selectively obtain a certain extracellular high-molecular product by culturing a microorganism transformed with a plasmid carrying foreign DNA fragment having genetic information of extracellular production of high-molecular substances which are metabolic products of another microorganisms. Such extracellular production has not successfully been done even when a transformant of Escherichia species, which is usually used as a host microorganism, is used.

U.S. Pat. No. 4,411,994 of W. Gilbert et al discloses a process for producing spcific proteins in bacteria and having them excreted from the bacterial cell. This process comprises inserting the DNA representing the desired non-bacterial protein or part of a protein by recombinant techniques into a plasmid or phage gene for either a periplasmic or an extracellular protein, hereinafter called a "carrier protein", transforming a bacterial host with the recombinant gene, and culturing the transformed host to excrete the protein. The process of this patent provides a means for producing a selected protein by employing a gene for a carrier protein which has a leader sequence of hydrophobic amino acids at its amino terminus.

Cell wall of *Escherichia coli* which has often been used for production of useful physiologically active substances, consists of three kinds of membrane: inner membrane, peptide glycan and outer membrane. The space between the inner and outer membrane is called the periplasmic space. The process of U.S. Pat. No. 4,411,994 has succeeded in the excretion of the products within the periplasmic space but not within the culture medium through the outer membrane or outside the bacterial host cell. In the present invention, by inserting the DNA having genetic information of extracellular production of high-molecular substances into the plasmid to obtain a hybrid plasmid and culturing the host transformed with the hybrid plasmid, it is possible to excrete useful physiologically active substances through the outer membrane and recover them directly from the culture medium. Thus, the present invention makes mass production of useful physiologically active substances possible, which has never been possible by the prior art process.

SUMMARY OF THE INVENTION

Therefore, an object of the present invention is to provide a novel plasmid with DNA carrying genetic information of extracellular production of high-molecular compounds, a method for construction of the plasmid, a novel microorganism carrying the plasmid and a method for culturing the microorganism.

A novel plasmid according to the present invention is one which provides a host with extracellular producibility of high-molecular substances such as xylanase and, which is constructed from a vector plasmid and a DNA fragment having genetic information of extracellular production of high-molecular substances such as xylanase and being obtained from a microorganism of the genus Bacillus.

The plasmid can be prepared by a process which comprises preparing, with a restriction enzyme, a chromosomal DNA fragment coding for extracellular production of xylanase, digesting a plasmid vector DNA with a restriction enzyme which does not interfere with the genetic information carried on the chromosomal DNA fragment, treating the chromosonal DNA fragment and the digested vector plasmid with DNA ligase to form a recombinant plasmid and isolating the recombinant plasmid.

A novel microorganism according to the present invention is one which belongs to the genus Escherichia, which contains the recombinant plasmid and which have extracellular producibility of high-molecular substances such as xylanase.

The present invention also provides a method for culturing the microorganism thus prepared to produce the high-molecular substances outside the bacterial cell, which comprises inoculating the microorganism in a culture medium containing a selected carbon source together with an inorganic salt necessary for the microorganism to grow, keeping on culturing the microorganism, after the concentration of the microorganism cells reached the maximum and until the production and accumulation of the high-molecular substances in the medium reach the maximum.

DETAILED DESCRIPTION OF THE INVENTION

Figure 1:
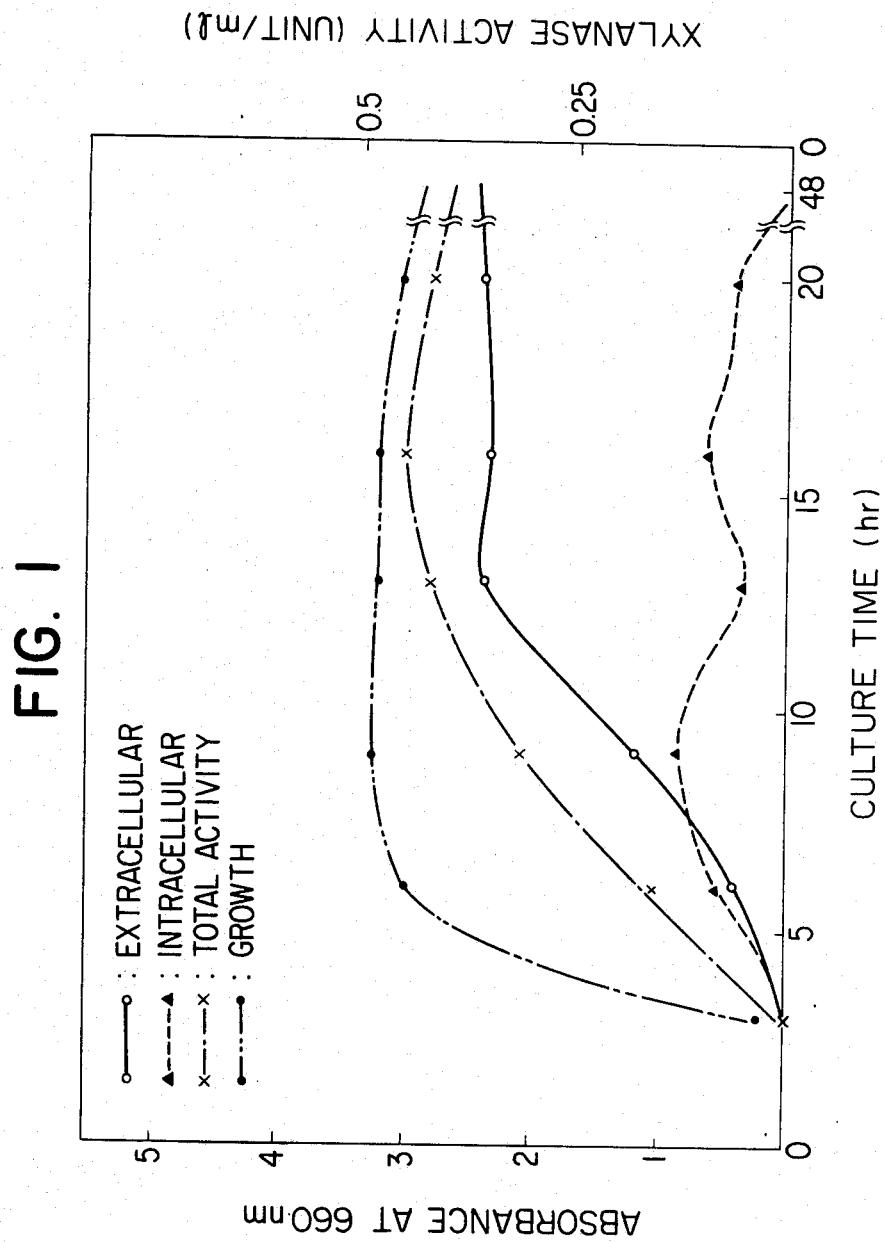
FIG. 1 and FIG. 2 show bacterial growth and xylanase production by *Escherichia coli* HB101(pCX311) of the present invention.

The term "high molecular substances" used in the specification and the claims of this application means useful physiologically active compounds including bacterial metabolic products such as enzyme proteins, antibiotics and the like, and biologically active proteins of mammalian origin.

The present invention will now be explained in detail.

(A) PLASMID AND CONSTRUCTION OF THE SAME

A novel plasmid of the present inveniton is one which is constructed by inserting a foreign DNA or an exogenote into a plasmid (extrachromosomal DNA or vector DNA), such as ColE$_1$, found in Escherichia cells.

Vector DNA which can be used in the present invention includes those isolated from natural sources, or those from which the DNA fragment unnecessary for self-reproduction has been deleted, such systems as ColE$_1$, pMB9, pBR322, pSC101, R6K and lambda phage.

Foreign DNA fragments or exogenotes which can be inserted into the vector DNA are the genes having genetic information of extracellular production or secretion of high-molecular substances, such as enzyme proteins, for example, xylanase, penicillinase, alkaline phosphatase, β-galactosidase, amylase, protease, β-glucanase, cellulase and the like.

Exogenotes or DNA fragments which can be used in the present invention include the genes having genetic information of extracellular production or secretion of high molecular substances and being obtained from a microorganism which belongs to, for example, the genus Bacillus.

One example of the microorganisms containing the DNA which has genetic information of extracellular xylanase production and which can be used in the present inveniton is Bacillus sp. C125.

Bacillus sp. C125 isolated from a soil sample collected in Tsurugashima, Saitama, Japan shows the following characteristic microbiological properties. An examinatin and classification of this strain were done according to "Aerobic Spore-forming Bacteria" (U.S. Department of Agriculture, Nov. 1952 by N. R. Smith, R. E. Gordon & F. E. Clark) and "Bergey's Manual of Determinative Bacteriology (1957)".

CHARACTERISTIC MICROBIOLOGICAL PROPERTIES (a) Morphology
(1) Rods, the size of which is 0.5–0.7 micron × 3.0–4.0 micron
(2) the spore formed is of oval type, the size of which is 0.6–0.8 micron × 1.0–1.2 micron, and the sporangium is swollen.
(3) Gram positive.
(b) Growth on Culture Medium

| Culture Medium | Growth | |
|---|---|---|
| | pH 7 | pH 10 |
| (1) Bouillon | grow | good |
| (2) Bouillon-agar | " | " |
| (3) Glucose-bouillon | slightly grow | " |
| (4) Glucose-bouillon-agar | " | " |
| (5) Tyrosine-agar | " | " |
| (6) Medium I | " | " |
| (7) Glucose-nitrate | grow | " |
| (8) Glucose-asparagine-agar | nil | " |
| (9) Medium-I + 5% NaCl | grow | " |

(c) Physiological Properties

| | pH 7 | pH 10 |
|---|---|---|
| (1) Nitrate reduction | no | almost nil |
| (2) Utilization of propionate | no | yes |
| (3) VP test | negative | negative |
| (4) Urease test | negative | neutral |
| (5) Hydrolysis of starch | positive | positive |
| (6) Hydrolysis of casein | positive | positive |
| (7) Growth condition | grow below pH 11.0 and below 55° C. | |
| (8) Growth under no-oxygen condition (on Medium-I) | no | slightly grow |

Summarizing the properties above, it is clear that the microorganism belongs to the genus Bacillus because it is an aerobic, spore-forming bacterium. We concluded that the microorganism Bacillus sp. C125 is a new strain of alkalophilic bacteria because it is clearly different from known bacteria in that it grows under the conditions of pH of below 11.0 and temperature of below 55° C.

For the purpose of the insertion of a foreign DNA into a vector DNA, any conventional methods can be used in the present invention. For instance, a chromosomal DNA is digested with a suitable restriction enzyme or endonuclease to obtain a foreign DNA fragment or an exogenote which is then mixed with a vector DNA which has been treated with the similar restriction enzyme, and the mixture is ligated by a suitable ligase. Thus, as described before, the novel plasmid of the present invention can be obtained by preparing, with a restriction enzyme, a DNA fragment coding for extracellular production of xylanase or the like, digesting a plasmid vector DNA with a restriction enzyme which does not interfere with genetic information carried on the DNA fragment, treating the DNA fragment and the digested vector plasmid with DNA ligase to construct a recombinant plasmid and isolating the recombinant plasmid by a conventional manner [see Bolivar et al Gene, 2, 95 (1977)].

Figure 4:
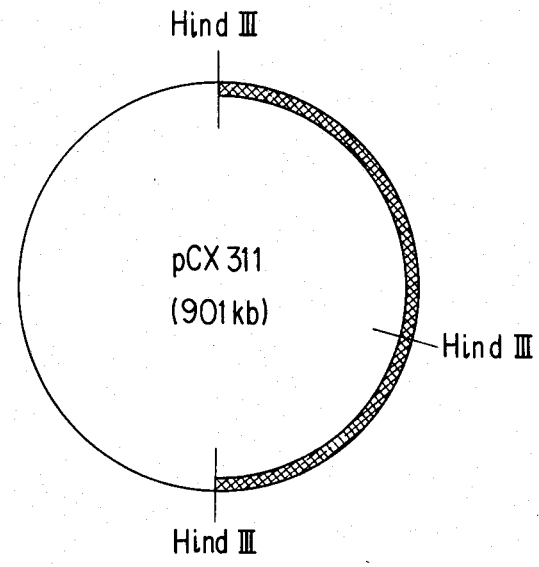
FIG. 4 shows the restriction enzyme cleavage map for the plasmid, pCX311.

Novel plasmid pCX311 can be constructed from Bacillus sp. C125 chromosomal DNA fragment and plasmid pBR322. Restriction enzyme map for plasmid pCX311 is shown in FIG. 4. As seen from FIG. 4, plasmid pCX311 is constructed from plasmid pBR322 into which the Bacillus sp. C125 chromosomal DNA coding for extracellular xylanase production is inserted between the Hind III restricted site of plasmid pBR322. Thus, plasmid pCX311 is a cyclic DNA molecule of about 9.01 kb, consisting of pBR322 DNA and the Bacillus sp. C125 DNA of about 4.0 kb.

(b) Preparation of Microorganism

The recombinant plasmid constructed from the chromosomal DNA fragment and the vector DNA plasmid is introduced into a host microorganism of the genus Escherichia by a conventional transformation technique. Cultivation is kept on until stabilized genotype is established, to obtain a transformant carrying both genotypes on the selected chromosomal DNA and on the vector DNA. For this purpose, a conventional, so called shot gun method can be used.

Typical host microorganism which can be used in the present invention is *Escherichia coli* HB101 which is a hybrid strain of *Escherichia coli* K-12 and *Escherichia coli* B.

The transformant, *Escherichia coli* HB101 (pCX311) which is prepared by introducing plasmid pCX311 into *Escherichia coli* HB101 has the same microbiological properties as those of the host, *Escherichia coli* HB101, except penicillin resistance and xylanase producibility [Molecular Cloning, A Laboratory Manual, p. 504 (1982), Genotype: F−, hsd S 20($r_B^-$, $m_B^-$), rec A13, ara-14, proA2, lacY1, galK2, rpsL20(Sm'), xyl-5 mtl-1,supE44λ−].

*Escherichia coli* HB101 (pCX311) is further characterized by the property of plasmid pCX311, that is, the extracellular xylanase producibility.

Figure 3:
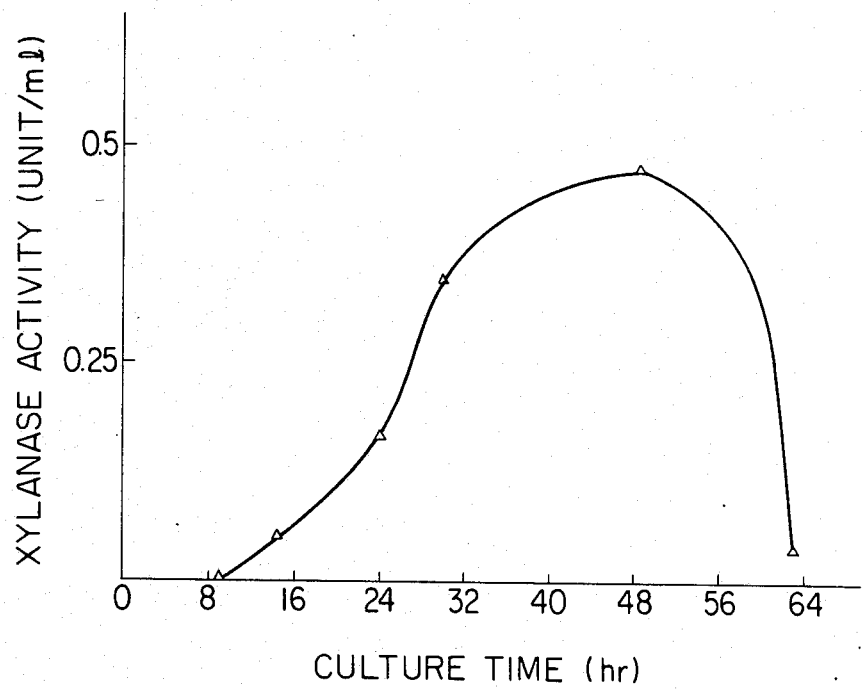
FIG. 3 shows xylanase production by Bacillus sp. C125.

The extracellular production of xylanase by *Escherichia coli* HB101 (pCX311), as shown in Examples described after, reaches more than 80% of total production including the intracellular production and remains after long cultivation. In contrast, extracellular production or activity of xylanase by Bacillus sp. C125, as shown in FIG. 3, reaches the maximum slowly and then, it drops rapidly. Thus, the extracellular production by Bacillus sp. C125 can not be compared with that by *Escherichia coli* HB101 (pCX311) of the present invention.

The present invention which provides *Escherichia coli* HB101 (pCX311) having extracellular producibility of enzyme proteins such as xylanase is not only novel but also inventive. *E. coli* HB101 (pCX311) can produce and secrete into the medium from the cells, in addition to large amounts of xylanase, large amounts of other enzyme proteins which can also be collected. More specifically, it has been discovered that *Escherichia coli* HB101 (pCX311) produces and secretes into the medium from the cells, as shown in Examples described after, large amounts of penicillinase, alkaline phosphatase, in addition to xylanase which have ever been observed only in the periplasmic space.

Such extracellular production by *Escherichia coli* HB101 (pCX311) demonstrates that the DNA of about 4000 nucleotide base pairs carried on plasmid pCX311 provides the host with the extracellular producibility of the metabolic products.

(c) Cultivation of the Microorganism

For culturing the transformant prepared in step (b), any culture media can be used which are suitable for the production of specific substances for which specific genetic information codes and which are suitable for growth of the microorganisms of the genus Escherichia. In the process of the present invention, it is necessary to culture the micrrorganism in a culture medium containing a selected carbon source together with an inorganic salt necessary for the microorganism to grow, and to keep on culturing the microorganism, after the concentration of the microorganism cells reached the maximum, and until the production and accumulation of the high-molecular substances in the media reach the maximum.

Examples of the inorganic salt which can be used in the present invention include sodium and potassium salts such as sodium chloride, sodium sulfate, potassium chloride and the like, among which sodium chloride is preferred. The media containing the selected carbon source together with the inorganic salt can contain such carbon source as glucose, sucrose, lactose, maltose, glycerol, bran, xylan and the like, such nitrogen source as ammonia water, ammonium salts and the like, inorganic ions and optionally such nutrient as amino acids, vitamin and the like. In the culture of *Escherichia coli* HB101 (pCX311), it is important and necessary to add to the medium the carbon source suitable for a selected product. The culture media which can be used in the present invention are those which use, as a basic medium, LB-broth (containing tryptone, yeast extract and NaCl), BPB-broth (Difco Laboratories; containing polypeptone, yeast extract and $K_2HPO_4$), nutrient broth (Difco 0001), tryptone-NaCl broth or the like.

Since more than 80% of total products remain in the intracellular fraction in a medium containing no inorganic salt, it is necessary to use a medium containing an inorganic salt in order that most products are secreted into the culture medium out of the cells. The amount of inorganic salt used is in the range of 0.5–3.0% by weight on the basis of the culture medium.

In the culture of *Escherichia coli* HB101 (pCX311), excellent results are obtained by the use of the LB-broth to which bran and/or xylan have been added as carbon sources, preferably in the amount each of 0.5% by weight on the basis of the culture medium.

Although culture conditions such as pH, temperature, oxygen supply or the like can be changed for the optimum growth of the microorganism of the genus Escherichia, it is necessary, in the present invention, to keep on culturing the microorganism, after the concentration of the microorganism cells reached the maximum, that is to say, after the latter logarithmic phase and until the production and accumulation of the high-molecular substances in the medium reach the maximum.

After the inoculation of the microorganism of the genus Escherichia in the medium, the cell concentration reaches the maximum for 5 to 20 hours and the production and accumulation of the high-molecular substances reach the maximum for 12 to 48 hours. Although pH of the culture mudium is not critical, it is preferred in the range of pH5–pH8, especially pH7. Thus, without further addition of inorganic salt necessary for the microorganism to grow, carbon sources and the like during cultivation, the microorganism produces large amounts of extracellular high-molecular substances which can conveniently be collected.

According to the culture method of the present invention, in addition to enzyme proteins, such high-molecular fermentation products as antibiotics, polysaccharides can be produced in a significant amount. This method can be applied to the cultivation of any microorganisms transformed with a plasmid carrying a foreign DNA coding for biologically active high-molecular substances such as hormone peptide (e.g. insulin) or interferon and the DNA coding for extracellular production or secretion of biologically active high-molecular substances, which leads to mass production of the high-molecular substances such as insulin, interferon and the like.

As explaind above, the present invention contributes to the industrial production of useful high-molecular substances.

Examples of microorganisms which may be used in this invention include (i) Bacillus sp. C125 and (ii) *Escherichia coli* HB101 (pCX311), all of which were deposited with the Fermentation Research Institute, Agency of Industrial Science and Technology, Ministry of International Trade and Industry, Japan, International Depository Authority (hereinafter referred to as "FERM") under the following accession numbers, respectively, FERM BP-469 and FERM BP-470 and are on deposit with FERM in an unrestricted deposit permitting the full access to the culture.

The depository and accession numbers of the above mentioned microorganisms are shown below:

| Microorganims | Depository | Accession No. |
| --- | --- | --- |
| (i) Bacillus sp. C125 | FERM | FERM BP-469 |
| (ii) *Escherichia coli* HB101 (pCX311) | FERM | FERM BP-470 |

The applicant will maintain the deposition of FERM BP-469 and FERM BP-470 in the unrestricted form until the end of the duration of a patent granted on this application if a patent is granted on this application, and thus said microorganism strains will be available to any third party at any time until the end of the duration of the patent granted on this application.

We will now explain, with reference to Examples, method for construction of the plasmid of the present invention, method for preparation of the transformant, *Escherichia coli* HB101 (pCX311), and the extracellular production of xylanase and so on by the transformant.

EXAMPLE 1

(1) Preparation of a chromosomal DNA having genetic information of xylanase producibility.

Alkalophilic Bacillus sp. C125 (FERM BP-469) having extracellular producibility of xylanase was cultured with shaking at 30° C. for 19 hours in the broth (containing 10.0 g of bran, 5.0 g of yeast extract, 5.0 g of polypeptone, 0.2 g of $MgSO_4 \cdot 7H_2O$, and 10 g of $Na_2CO_3$ in one liter of water and adjusted to pH 6.0). The cells in the latter logarithmic phase were collected, from which a chromosomal DNA was extracted by the phenol extraction method and purified to obtain 5 mg of the chromosomal DNA.

(2) Insertion of chromosomal DNA fragment into vector DNA.

The chromosomal DNA (10 μg) obtained in step (1) was digested with the restriction enzyme Hind III at 37° C. for 5, 10, 20, 30 and 60 minutes to obtain DNA fragments.

Plasmid pBR322 [Bethesda Research Laboratories, U.S.A., tetracyclin resistant (Tet$^r$) and ampicillin resistant (Amp$^r$)] used as the vector was cut with Hind III, then heated at 65° C. for 5 minutes, and then mixed with the DNA fragments. The mixture was treated with T$_4$ phage DNA ligase at 10° C. for 24 hours and then heated at 65° C. for 5 minutes.

Three times volume of ethanol was added to the mixture. Plasmids carrying the chromosomal DNA fragments were precipitated and collected.

(3) Transformation of the microorganism with plasmids having gene for extracellular production of xylanase.

*Escherichia coli* HB101 which is a hybrid strain of *Escherichia coli* K-12 and *Escherichia coli* B, was inoculated in 10 ml of LB-broth [containing 10 g of tryptone (Difco Laboratories, Detroit, Mich.), 5 g of yeast extract, 1 g of glucose and 10 g of NaCl in one liter of deionized water; pH was adjusted to 7.0] and cultured at 37° C. with shaking until the latter logarithmic phase. The cells were collected and suspended in an ice-cold $CaCl_2$ solution of 0.03M (final concentration) to obtain competent cells. The cell suspension and the plasmid solution obtained in step (2) were combined and kept on ice for 60 minutes. The mixture was heated to 42° C. for 1 to 2 minutes to introduce the plasmid DNA into the cells. This cell suspension was inoculated in fresh LB-broth and cultured at 37° C. for 3 to 5 hours with shaking. The cells were collected and washed to obtain transformants, from which *Escherichia coli* HB101 (pCX311) (FERM BP-470) having extracellular producibility of xylanase and penicillinase was isolated.

EXAMPLE 2

Perparation and purification of plasmid pCX311

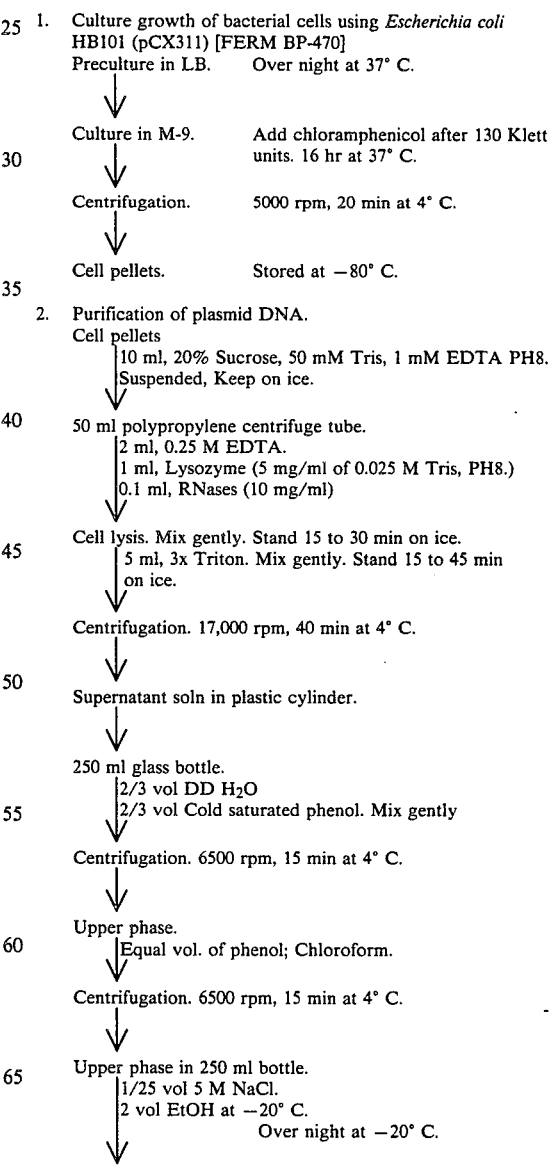

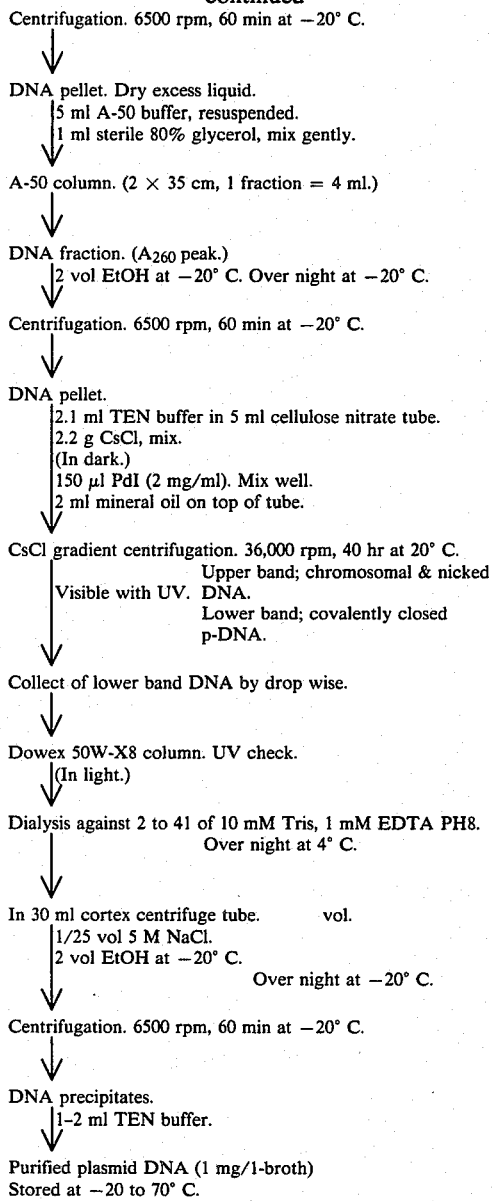

-continued
Centrifugation. 6500 rpm, 60 min at −20° C.
↓
DNA pellet. Dry excess liquid.
  5 ml A-50 buffer, resuspended.
  1 ml sterile 80% glycerol, mix gently.
↓
A-50 column. (2 × 35 cm, 1 fraction = 4 ml.)
↓
DNA fraction. ($A_{260}$ peak.)
  2 vol EtOH at −20° C. Over night at −20° C.
↓
Centrifugation. 6500 rpm, 60 min at −20° C.
↓
DNA pellet.
  2.1 ml TEN buffer in 5 ml cellulose nitrate tube.
  2.2 g CsCl, mix.
  (In dark.)
  150 μl PdI (2 mg/ml). Mix well.
  2 ml mineral oil on top of tube.
↓
CsCl gradient centrifugation. 36,000 rpm, 40 hr at 20° C.
  Visible with UV.  Upper band; chromosomal & nicked DNA.
                    Lower band; covalently closed p-DNA.
↓
Collect of lower band DNA by drop wise.
↓
Dowex 50W-X8 column. UV check.
  (In light.)
↓
Dialysis against 2 to 4 l of 10 mM Tris, 1 mM EDTA PH8.
  Over night at 4° C.
↓
In 30 ml cortex centrifuge tube.    vol.
  1/25 vol 5 M NaCl.
  2 vol EtOH at −20° C.
              Over night at −20° C.
↓
Centrifugation. 6500 rpm, 60 min at −20° C.
↓
DNA precipitates.
  1-2 ml TEN buffer.
↓
Purified plasmid DNA (1 mg/1-broth)
Stored at −20 to 70° C.

EXAMPLE 3

*Escherichia coli* HB101 (pCX311) (FERM BP-470) obtained in step (3) of Example 1 was inoculated in 500 ml-flasks containing 100 ml of LB-broth (containing 10 g of tryptone, 5 g of yeast extract, 1 g of glucose, 2 g of glycerol, 10 g of NaCl and 10 mg of penicillin in one liter of water) containing 0.5% xylan and cultured at 37° C. with shaking. Cell growth was measured by optical density at 660 nm. Enzyme activity was assayed as follows: 0.05 ml of the culture fluid, 0.1 ml of xylan solution (Seikagaku Kogyo, Japan) and 0.1 ml of 0.2M Tris-malate buffer of pH8.0 were mixed and heated at 40° C. for 10 minutes. One ml of DNS (3.5-dinitrosalicylic acid) was added to the mixture, which was then heated at 100° C. for 5 minutes. Four ml of water was added to the mixture. Absorbance at 510 nm was measured. One unit of xylanase reduces one mg of xylose per one minute.

FIG. 1 shows extracellular production or secretion of xylanase by *Escherichia coli* HB101 (pCX311) cultured in the LB-broth containing 0.5% xylan.

As shown in FIG. 1, cell growth of the transformant reached the maximum after 9 to 12 hours cultivation and extracellular xylanase activity began to increase after 6 hours and reached the maximum (about 0.35 unit/ml) after 13 hours cultivation.

Figure 2:
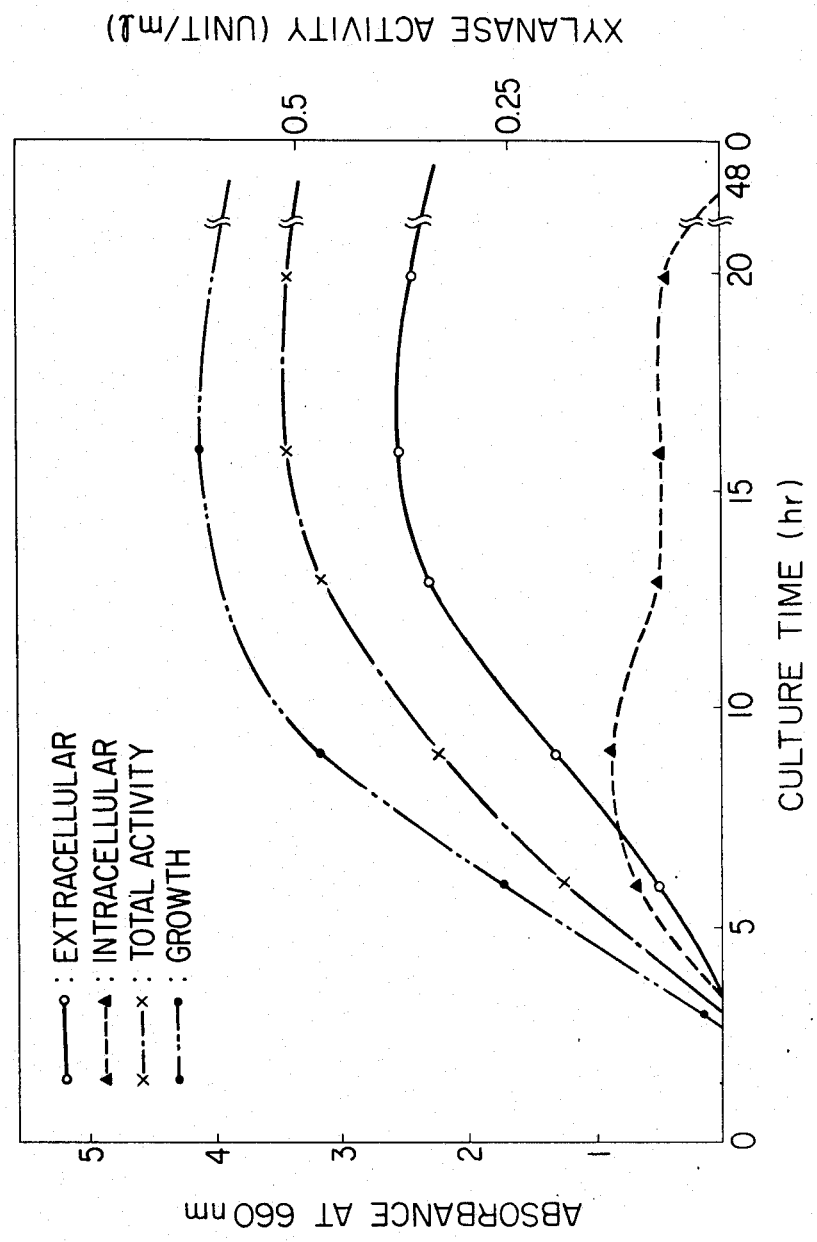

Extracellular xylanase produced was very stable and, as shown in FIG. 1, the production was kept high even after 48 hours cultivation and reached more than 80% of total enzyme production. In contrast, intracellular xylanase production was detected a little at an early phase (after 9 hours cultivation). But, the maximum was only 0.13 unit/ml or about 10% of total enzyme production and furthermore, the intracellular production decreased gradually. FIG. 2 shows xylanase production by *Escherichia coli* HB101 (pCX311) cultured in the LB-broth containing 0.5% bran instead of xylan. FIG. 2 shows the similar tendency as observed in FIG. 1. As a comparison, Bacillus sp. C125 (FERM BP-469) which is a DNA donor was cultured and xylanase activity was assayed.

Bacillus sp. C125 was inoculated in 500 ml-flasks containing 100 ml of the medium (which contained 10.0 g of xylan, 5.0 g of yeast extract, 5.0 g of polypeptone, 1.0 g of $K_2HPO_4$, 0.2 g of $MgSO_4.7H_2O$ and 10 g of $Na_2CO_3$ in one liter of water and was adjusted to pH 6.0) and cultured at 37° C. with shaking. Extracellular xylanase activity in the culture fluid was observed every eight hours. It began to increase after eight hours cultivation and reached the maximum (about 0.5 unit/ml) after 48 hours, but it decreased quickly (FIG. 3).

[IDENTIFICATION OF XYLANASE]

Ammonium sulfate was added to the culture fluid of the transformant obtained in step (3) of Example 1. The precipitate salted out was dissolved in water and the solution was dialyzed overnight against running water. The dialyzate was adsorbed on a CM-cellulose column equilibrated with 20 mM phosphoric acid-monosodium phosphate buffer of pH 4.5. Elution was done by applying a linear gradient of 0.1-0.7M sodium chloride. Xylanase was eluted with about 0.4M sodium chloride. The fractions exhibited xylanase activity were combined and applied on a Sephadex G-100 gel filtration to obtain purified xylanase.

Similarly, the culture fluid of Bacillus sp. C125 (FERM BP-469) was treated to obtain purified xylanase.

For the identification of *Escherichia coli* HB101 (pCX311) xylanase with Bacillus sp. C125 xylanase, effects of pH on activity, ultracentrifugal analysis, electrophoresis and estimation of molecular weight of each xylanase were examined. As a result, both the enzymes were identical with each other as shown below.

Figure 5:
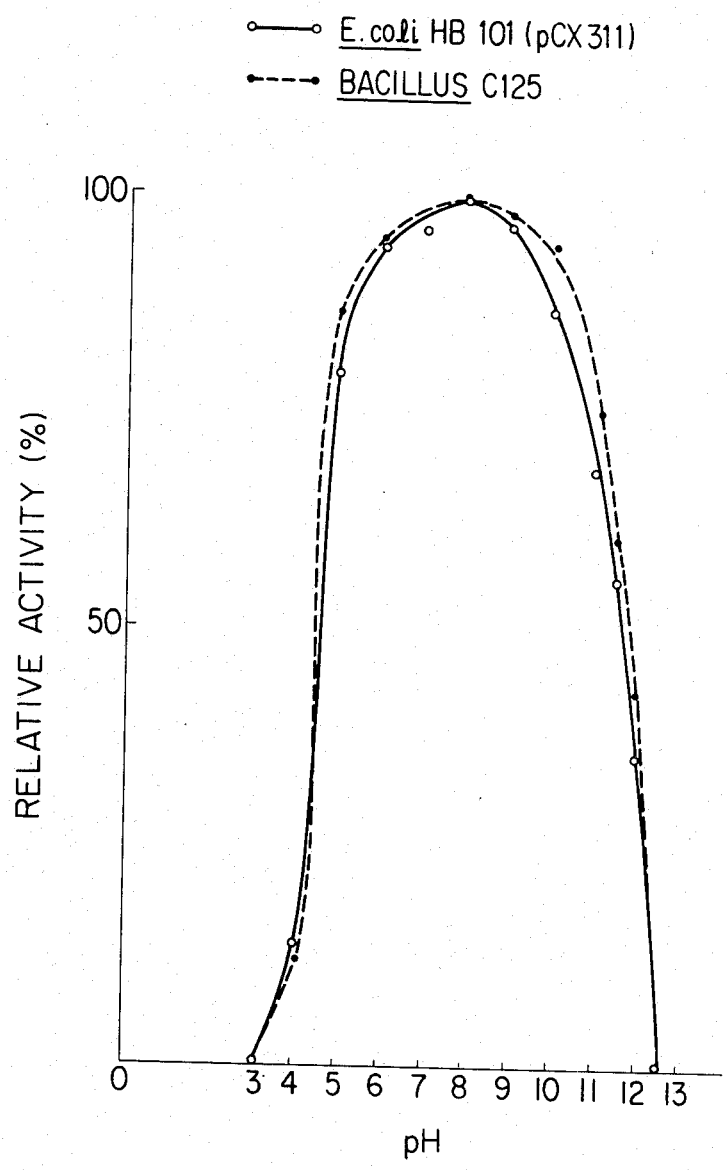
FIG. 5 shows the identity of pH activity of xylanase produced by *Escherichia coli* HB101(pCX311) with that produced by Bacillus sp. C125.

(a) Acetate (pH 4-5), Tris-malate (pH 5-8), Tris-HCl (pH 7-9), and glycine-NaOH (pH 9-11) were prepared. Using these buffer solutions, effects of pH on activity was examined. Results are shown in FIG. 5 which exhibits the identification of both the enzymes on pH activity.

(b) Ultracentrifugal analysis showed that both the enzymes had single peak of about 3.5S of sedimentation coefficient.

(c) Desk electrophoresis at pH 8.3 showed that both the enzymes had single band. Electrofocusing by Ampholine showed single peak. Isoelectric point of both the enzymes was pH6.3.

(d) Estimation of molecular weight of the enzymes was done by SDS-polyacrylamide method. Estimated molecular weight of both the enzymes was about 40,000.

EXAMPLE 4

*Escherichia coli* HB101, *Escherichia coli* HB101 (pBR322) and *Escherichia coli* HB101 (pCX311) (FERM BP-470) were cultured in the same, xylan-containing LB-broth as used in Example 2 at 37° C. with shaking for 20 hours (penicillinase) or for 15 hours (alkaline phosphatase and β-galactosidase). Enzyme activities of alkaline phosphatase and β-galactosidase were measured by optical density at 420 nm. Results are given in Table 1.

TABLE 1

| Micro- | | Activity (U/ml) | | |
|---|---|---|---|---|
| organism | Products | Extracellular | Intracellular | Total |
| E. coli HB101 | Alkaline phosphatase | 0.02 (2%) | 1.31 (98%) | 1.33 (100%) |
| | β-Galactosidase | 0.03 (2%) | 1.20 (98%) | 1.23 (100%) |
| E. coli HB101 (pBR322) | Alkaline phosphatase | 0.01 (2%) | 0.47 (98%) | 0.48 (100%) |
| | β-Galactosidase | 0.00 (0%) | 0.80 (100%) | 0.80 (100%) |
| | Penicillinase | 0.20 (3%) | 9.52 (97%) | 9.72 (100%) |
| E. coli HB101 (pCX311) | Alkaline phosphatase | 0.30 (60%) | 0.20 (40%) | 0.50 (100%) |
| | Penicillinase | 6.25 (77%) | 1.91 (23%) | 8.16 (100%) |

EXAMPLE 5

Effects of inorganic salts in the media on xylanase production by *Escherichia coli* HB101 (pCX311) (FERM BP-470) were examined. The same medium as that used in Example 3 was used as a basic medium. The microorganism was cultured for 14 or 20 hours in the basic medium to which varrious inorganic salts had been added. Results are given in Table 2.

TABLE 2

| Time (hrs.) | In- organic salt | Concent- ration of inorganic salt (M) | Xylanase activity (U/ml) | | |
|---|---|---|---|---|---|
| | | | Extracellular | Intracellular | Total |
| 14 | none | — | 0 | 0 | 0 |
| | NaCl | 0.08 | 0.07 | 0.11 | 0.18 |
| | " | 0.16* | 0.21 | 0.10 | 0.31 |
| | " | 0.32 | 0.38 | 0.10 | 0.48 |
| | " | 0.48 | 0.15 | 0.10 | 0.25 |
| | KCl | 0.16 | 0.25 | 0.12 | 0.37 |
| 20 | none | — | 0 | 0 | 0 |
| | NaCl | 0.08 | 0.06 | 0.07 | 0.13 |
| | " | 0.16 | 0.28 | 0.04 | 0.32 |
| | " | 0.32 | 0.40 | 0.13 | 0.53 |
| | " | 0.48 | 0.25 | 0.10 | 0.35 |
| | KCl | 0.16 | 0.28 | 0.02 | 0.30 |

*0.16 M NaCl corresponds to 1% by weight.

What we claim is:

1. A recombinant plasmid which is capable of inducing the extracellular secretion of xylanase in *Escherichia coli* transformed with said plasmid and which is obtained by inserting a chromosomal DNA fragment of Bacillus sp. C125 coding for extracellular secretion of xylanase, at restriction sites for a vector plasmid DNA.

2. The plasmid of claim 1, wherein the vector plasmid is plasmid pBR322.

3. The plasmid of claim 1, wherein the plasmid is plasmid pCX311.

4. A method of construction of a plasmid which is a recombinant plasmid capable of inducing the extracellular secretion of xylanase in *Escherichia coli* transformed with said plasmid and which is obtained by inserting a chromosomal DNA fragment of Bacillus sp. C125 coding for extracellular secretion of xylanase, at restriction sites of a vector plasmid DNA, which comprises the steps of:
(a) preparing with a first restriction enzyme, a chromosomal DNA fragment coding for extracellular secretion of xylanase, from Bacillus sp. C125,
(b) digesting a vector plasmid DNA with a second restriction enzyme which does not interfere with the genetic information carried on the chromosomal DNA fragment;
(c) treating said chromosomal DNA fragment and said digested vector plasmid DNA with DNA ligase to form the recombinant plasmid DNA, and
(d) isolating the recombinant plasmid DNA.

5. The method of claim 4 wherein the first and second restriction enzymes are restriction enzyme Hind III.

6. The method of claim 4, wherein the vector plasmid is pBR322.

7. The method of claim 4, wherein the recombinant plasmid is plasmid pCX311.

8. *Escherichia coli* HB101 which has been transformed with plasmid pCX311 and which is capable of extracellular secretion of xylanase.

9. A method of cultivating a transformant which comprises:
(a) inoculating the transformant carrying a recombinant plasmid which is capable of inducing the extracellular secretion of xylanase in *Escherichia coli* transformed with said plasmid, and which is obtained by inserting a chromosomal DNA fragment of Bacillus sp. C125 coding for extracellular secretion of xylanase, at restriction sites of a vector plasmid DNA, in a medium containing a selected carbon source together with an inorganic salt which is a member selected from the group consisting of sodium salts and potassium salts;
(b) keeping on culturing the transformant after the concentration of the transformant cells reached the maximum and the production and accumulation of xylanase in the medium reached the maximum.

10. The method of claim 9, wherein the inorganic salt is sodium chloride or potassium chloride.

11. The method of claim 9, wherein the inorganic salt is used in an amount of 0.5 to 3.0% by weight on the basis of the weight of the medium.

12. The method of claim 9, wherein the carbon source is bran or xylan.

13. The method of claim 9, wherein the transformant is cultured for 12 to 48 hours.

14. The method of claim 9, wherein the transformant is *Escherichia coli* HB101 which has been transformed with plasmid pCX311 and is capable of extracellular secretion of xylanase.

15. The method of claim 9, wherein the inorganic salt is sodium chloride or potassium chloride and is used in an amount of 0.5 to 3.0% by weight on the basis of the weight of the medium, the carbon source is bran or xylan, and the transformant is cultured for 12 to 48 hours.

* * * * *